(12) United States Patent
Baracaldo Angel et al.

(10) Patent No.: US 11,113,419 B2
(45) Date of Patent: Sep. 7, 2021

(54) SELECTIVE ENFORCEMENT OF PRIVACY AND CONFIDENTIALITY FOR OPTIMIZATION OF VOICE APPLICATIONS

(71) Applicant: International Business Machines Corporation, Armonk, NY (US)

(72) Inventors: Nathalie Baracaldo Angel, San Jose, CA (US); Heiko H. Ludwig, San Francisco, CA (US); Robert J. Moore, San Jose, CA (US); Guangjie Ren, Belmont, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/681,048

(22) Filed: Nov. 12, 2019

(65) Prior Publication Data

US 2020/0082123 A1    Mar. 12, 2020

Related U.S. Application Data

(63) Continuation of application No. 15/685,002, filed on Aug. 24, 2017, now Pat. No. 10,540,521.

(51) Int. Cl.
*G06F 21/62* (2013.01)
*G10L 15/26* (2006.01)
(Continued)

(52) U.S. Cl.
CPC .......... *G06F 21/6254* (2013.01); *G06F 3/167* (2013.01); *G06F 21/60* (2013.01);
(Continued)

(58) Field of Classification Search
CPC ..... G10L 15/26; G06F 21/60; G06F 21/6245; G06F 21/6254
See application file for complete search history.

(56) References Cited

U.S. PATENT DOCUMENTS 7,383,183 B1   6/2008   Davis
8,140,326 B2   3/2012   Chen
(Continued)

OTHER PUBLICATIONS

List of IBM Patents or Patent Applications Treated as Related, Filed Nov. 12, 2019, 2 pages.
(Continued)

*Primary Examiner* — James R Turchen
(74) *Attorney, Agent, or Firm* — Aaron N. Pontikos

(57) ABSTRACT

A computer-implemented method includes identifying a plurality of protected pieces from a conversation. The computer-implemented method further includes generating one or more confidence scores for each protected piece, wherein a confidence score is a degree of associativity between a protected piece and a type of sensitive information. The computer-implemented method further includes determining that the protected piece is associated with the type of sensitive information. The computer-implemented method further includes determining a type of protection action for each protected piece in the plurality of protected pieces. The computer-implemented method further includes performing the type of protection action for each protected piece in the plurality of protected pieces to form a modified conversation that is devoid of the sensitive information. A corresponding computer system and computer program product are also disclosed.

17 Claims, 3 Drawing Sheets

(51) Int. Cl.

| | |
|---|---|
| G10L 15/08 | (2006.01) |
| G10L 21/0364 | (2013.01) |
| H04K 1/04 | (2006.01) |
| H04K 1/06 | (2006.01) |
| G10L 21/0208 | (2013.01) |
| G16H 10/60 | (2018.01) |
| G06F 21/60 | (2013.01) |
| H04L 29/06 | (2006.01) |
| G06Q 30/02 | (2012.01) |
| G06F 3/16 | (2006.01) |
| G10L 15/06 | (2013.01) |
| H04W 12/02 | (2009.01) |
| G10L 15/22 | (2006.01) |
| G10L 17/08 | (2013.01) |
| G10L 21/00 | (2013.01) |

(52) U.S. Cl.
CPC ..... *G06F 21/6245* (2013.01); *G06Q 30/0201* (2013.01); *G10L 15/08* (2013.01); *G10L 15/26* (2013.01); *G10L 21/0208* (2013.01); *G10L 21/0364* (2013.01); *G16H 10/60* (2018.01); *H04K 1/04* (2013.01); *H04K 1/06* (2013.01); *H04L 63/0414* (2013.01); G10L 15/063 (2013.01); G10L 15/22 (2013.01); G10L 17/08 (2013.01); G10L 21/00 (2013.01); H04W 12/02 (2013.01)

(56) References Cited

U.S. PATENT DOCUMENTS

| | | | |
|---|---|---|---|
| 8,229,742 | B2 | 7/2012 | Zimmerman |
| 8,244,531 | B2 | 8/2012 | Erhart |
| 8,463,606 | B2 | 6/2013 | Scott |
| 9,253,304 | B2 | 2/2016 | Bhogal |
| 9,307,084 | B1* | 4/2016 | Pycko ............... H04M 3/5166 |
| 9,514,741 | B2 | 12/2016 | Jost |
| 9,544,438 | B1* | 1/2017 | Andraszek ............ G10L 21/06 |
| 10,002,639 | B1* | 6/2018 | Gaeta .................... G10L 15/02 |
| 10,121,493 | B2* | 11/2018 | Aravamudan ........ G10L 15/22 |
| 10,313,520 | B2* | 6/2019 | Dwyer ................ G06F 40/279 |
| 2005/0223412 | A1* | 10/2005 | Nadalin ............... H04L 63/126 726/3 |
| 2007/0244700 | A1* | 10/2007 | Kahn .................... G10L 15/22 704/235 |
| 2008/0033757 | A1 | 2/2008 | Kozloff |
| 2008/0221882 | A1* | 9/2008 | Bundock ................ G10L 15/26 704/235 |
| 2008/0228496 | A1* | 9/2008 | Yu ........................ G10L 15/24 704/275 |
| 2010/0082342 | A1 | 4/2010 | Erhart |
| 2010/0162355 | A1 | 6/2010 | Zimmerman |
| 2011/0010173 | A1 | 1/2011 | Scott |
| 2011/0218798 | A1* | 9/2011 | Gavalda ................ G10L 17/00 704/201 |
| 2012/0143596 | A1 | 6/2012 | Bhogal |
| 2012/0150537 | A1* | 6/2012 | Abe .................... G06F 16/7844 704/235 |
| 2013/0231930 | A1* | 9/2013 | Sanso ..................... G10L 15/26 704/235 |
| 2013/0266127 | A1* | 10/2013 | Schachter ........... H04M 3/5175 379/88.01 |
| 2014/0032219 | A1* | 1/2014 | Lerner .................... G10L 25/48 704/270.1 |
| 2014/0172424 | A1 | 6/2014 | Grokop |
| 2014/0207442 | A1* | 7/2014 | Ganong, III ............ G10L 15/30 704/201 |
| 2014/0278426 | A1 | 9/2014 | Jost |
| 2014/0316764 | A1* | 10/2014 | Ayan ....................... G10L 15/22 704/9 |
| 2015/0089357 | A1* | 3/2015 | Vandervort ........... G06F 40/166 715/256 |
| 2015/0149167 | A1* | 5/2015 | Beaufays ................ G10L 15/26 704/235 |
| 2015/0161406 | A1* | 6/2015 | Fox ..................... G06F 21/6245 726/27 |
| 2015/0180902 | A1* | 6/2015 | Biswas .................. H04W 12/02 726/1 |
| 2016/0063269 | A1* | 3/2016 | Liden .................. G06F 21/6254 726/26 |
| 2016/0155445 | A1* | 6/2016 | Selfridge ............ G10L 15/1822 704/249 |
| 2016/0364963 | A1* | 12/2016 | Matsuoka ................ G10L 25/51 |
| 2016/0379639 | A1* | 12/2016 | Weinstein ........... G06F 21/6254 704/235 |
| 2017/0034200 | A1* | 2/2017 | Costin ................ G06F 16/24578 |
| 2017/0076713 | A1* | 3/2017 | Gildein, II ............... H04N 7/15 |
| 2017/0104756 | A1* | 4/2017 | Rosenthal ............... H04L 63/20 |
| 2017/0126523 | A1* | 5/2017 | Chen ..................... H04L 41/069 |
| 2018/0082020 | A1* | 3/2018 | Rajagopal ............. G16H 10/60 |
| 2018/0082059 | A1* | 3/2018 | Bender ................ H04L 63/1433 |
| 2018/0096695 | A1* | 4/2018 | Kraemer ................ G10L 21/06 |
| 2018/0218085 | A1* | 8/2018 | Price ..................... G06F 40/134 |
| 2018/0241703 | A1* | 8/2018 | Feuz ....................... H04L 51/16 |
| 2018/0322106 | A1* | 11/2018 | Roks .................... G06F 3/04842 |
| 2018/0330714 | A1* | 11/2018 | Paulik ..................... G10L 15/16 |
| 2018/0367561 | A1* | 12/2018 | Giventai, I .......... H04L 63/1408 |
| 2019/0005952 | A1* | 1/2019 | Kruse .................... G10L 25/51 |
| 2019/0042568 | A1* | 2/2019 | Balabine ................ G06F 40/30 |
| 2019/0066686 | A1 | 2/2019 | Baracaldo Angel |

OTHER PUBLICATIONS

Caliskan-Islam, Aylin, "Stylometric Fingerprints and Privacy Behavior in Textual Data", PhD Thesis, Drexel University, May 2015, 170 pages.

Kumar et al., "Sound Shredding: Privacy Preserved Audio Sensing", HotMobile'15, Feb. 12-13, 2015, Santa Fe, New Mexico, pp. 135-140.

Parthasarathi et al., "Wordless Sounds: Robust Speaker Diarization Using Privacy-Preserving Audio Representations", IDIAP Research Report, IDIAP Research Institute, Sep. 2012, 15 pages.

Pathak et al., "Privacy-preserving speech processing: cryptographic and string-matching frameworks show promise", IEEE Signal Processing Magazine, vol. 30, Issue: 2, Mar. 2013, pp. 62-74.

Senior et al., "Privacy Protection and Face Recognition", Handbook of Face Recognition, Second Edition, © Springer-Verlag London Limited 2011, pp. 671-691.

Smaragdis et al., "A Framework for Secure Speech Recognition", IEEE 2007 International Conference on Acoustics, Speech, and Signal Processing (ICASSP 2007), Apr. 15-20, 2007, Honolulu, Hawaii, 10 pages.

Wyatt et al., "Capturing Spontaneous Conversation and Social Dynamics: A Privacy-Sensitive Data Collection Effort", IEEE 2007 International Conference on Acoustics, Speech, and Signal Processing (ICASSP 2007), Apr. 15-20, 2007, Honolulu, Hawaii, 4 pages.

Wyatt et al., "Conversation Detection and Speaker Segmentation in Privacy-Sensitive Situated Speech Data", www.dannywyatt.com/pubs/Wyatt-Interspeech07.pdf, Interspeech 2007, 4 pages.

* cited by examiner

SELECTIVE ENFORCEMENT OF PRIVACY AND CONFIDENTIALITY FOR OPTIMIZATION OF VOICE APPLICATIONS

BACKGROUND

The present invention relates generally to the field of information privacy and confidentiality, and more particularly to protecting sensitive information collected during verbal communications.

Information privacy (i.e., data privacy or data protection) is the relationship between the collection and dissemination of data, technology, public expectation of privacy, and the legal and political issues that dictate what is considered to be private information. Privacy concerns arise whenever personally identifiable information or other sensitive information is collected, stored, used, or otherwise disseminated. Some contexts where information privacy may arise include healthcare information, criminal information, financial information, address information, internet usage, and location based services (e.g., geo-location applications).

Voice application devices are devices that record and/or otherwise communicate with the human voice. Voice application devices can be found in computer operating systems, commercial software for computing devices, mobile phones, and automobiles. Examples of voice application devices include voice command devices (VCD's), monitoring devices, and companion devices, such as humanoid robots. Voice application devices may be speaker dependent or speaker independent. The latter such devices can respond to multiple voices, regardless of an individual's speech prosody characteristics. Current voice application devices are not only capable of receiving voice commands, but are further capable of responding, providing feedback, or otherwise generally imitating a natural voice conversation.

SUMMARY

A computer-implemented method includes identifying a plurality of protected pieces from a conversation, wherein each protected piece in the plurality of protected pieces corresponds to a portion of the conversation that includes sensitive information. The computer-implemented method further includes generating one or more confidence scores for each protected piece in the plurality of protected pieces, wherein a confidence score is a degree of associativity between a protected piece and a type of sensitive information. The computer-implemented method further includes determining that the protected piece is associated with the type of sensitive information based, at least in part, on the confidence score exceeding a given threshold level. The computer-implemented method further includes determining a type of protection action for each protected piece in the plurality of protected pieces based, at least in part, on the type of sensitive information associated with the protected piece. The computer-implemented method further includes performing the type of protection action for each protected piece in the plurality of protected pieces to form a modified conversation, wherein the modified conversation is devoid of the sensitive information. A corresponding computer system and computer program product are also disclosed.

DETAILED DESCRIPTION

Figure 1:
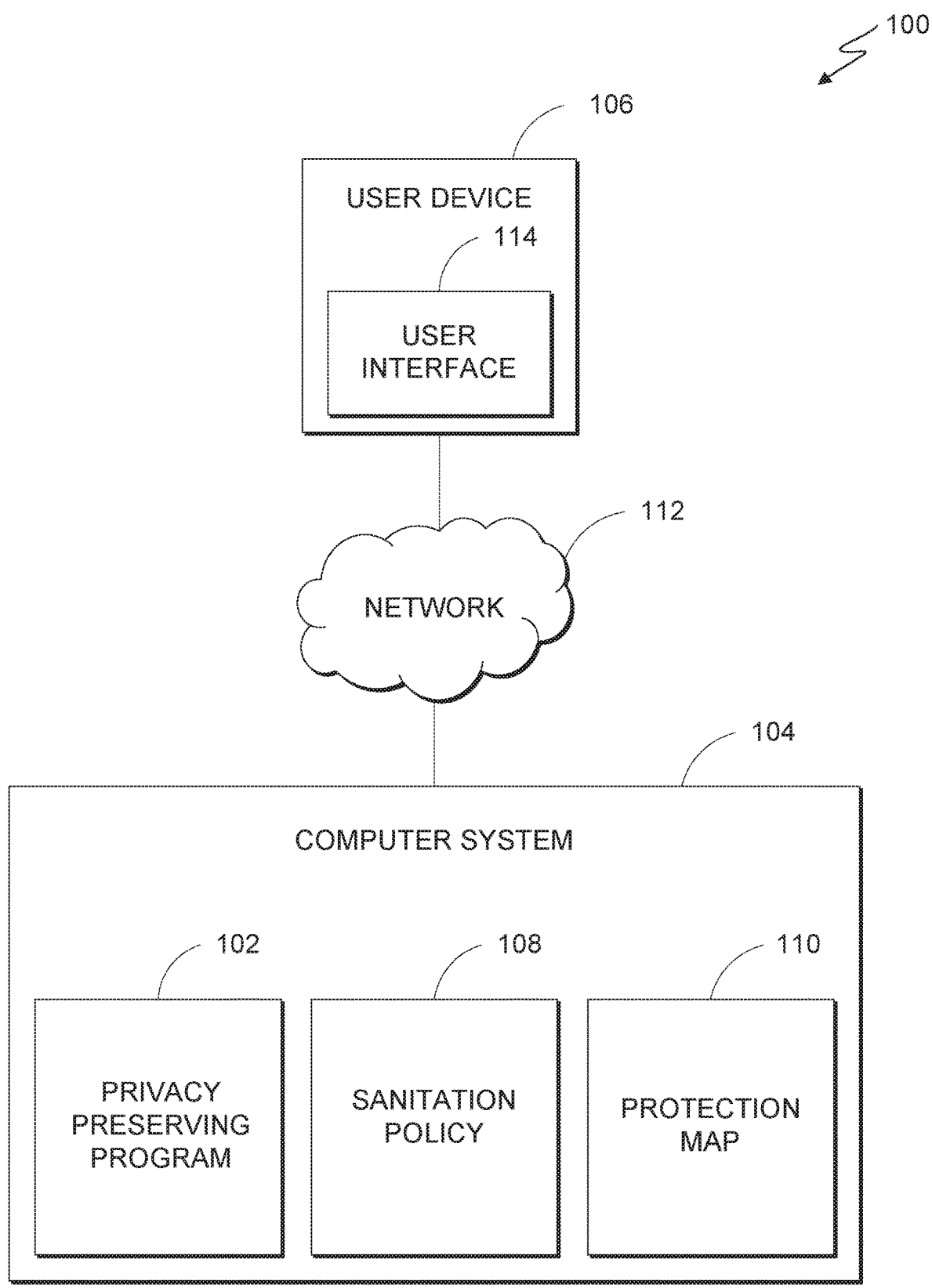
FIG. 1 is a functional block diagram of a computing environment suitable for operation of a privacy preserving program.

Generally, sensitive information (i.e., personal, private, or confidential information) is any information that requires protection against unwarranted disclosure. The protection of sensitive information may be required for legal or ethical reasons, personal privacy, or proprietary reasons. Examples of types of sensitive information include, but are not limited to social security numbers, medical history, political affiliation, addresses, phone numbers, client data, salary data, product specifications, and business plans. Accordingly, access to sensitive information should also be safeguarded.

There are no bright line rules for determining what an individual considers to be sensitive information. In some instances, what is deemed to be sensitive information is relatively straight forward. For example, the Health Insurance Portability and Accountability Act (HIPPA) of 1996 is a piece of United States legislation that provides data privacy and security provisions for safeguarding medical information. Similarly, the Telecommunications Act of 1996 provides for the Federal Communications Commission (FCC) authority to regulate how customer proprietary network information (CPNI) can be used, as well as enforce related consumer information privacy provisions (e.g., providing customer information to third-party marketing firms or sharing information during phone conversations with customer service representatives). However, in many instances, what is deemed to be sensitive information is highly subjective. Certain types of information may be considered sensitive in different contexts. For example, an individual may be willing to share medical history with a physician, but not with an accountant. Furthermore, what is considered to be sensitive information to one party may not be sensitive to another party. For example, a startup company makes an announcement that a new customer is purchasing their product. However, another startup company refrains from revealing the identity of a new customer in order to avoid potential targeting of the customer by competitors.

Information privacy (i.e., data privacy or data protection) concerns are becoming increasingly prevalent with the advent of new technologies. Embodiments of the present invention recognize that voice application devices are a relatively new and growing technology that present unique information security problems. More specifically, the collection, storage, or dissemination of information by voice application devices poses a broad range of information privacy and confidentiality issues.

Voice application devices include voice command devices (VCD's), monitoring devices, and companion robots. VCD's operate based on verbal communications, thus eliminating the need for physical interactions with a device. Some VCD's are active intermittently (activation is based on physical user action). For example, a user physically activates a VCD by pushing a button located on the VCD. Upon activating the VCD, the VCD may actively listen for verbal communications for 30 seconds. At the end of the 30 second time period, the VCD will become inactive. Other VCD's are active continuously (activation is based on a verbal trigger). For example, an individual can give a verbal command to a VCD to turn on the lights upon entering his home without requiring any prior physical activation of the device. Monitoring devices (i.e., ever-listening devices) listen to verbal conversations (e.g., a child safety monitoring device). Companion robots (i.e., virtual companions) include hardware and software applications designed to give companionship to a person, as well as provide medical or other functional assistance to various individuals, such as the elderly.

Voice application devices also have the ability to record verbal communications. In some instances, the recorded verbal communications are further stored by the voice applications devices themselves. In other instances, the recorded verbal communications are stored externally (e.g., a remote database or the cloud). Current methods for protecting sensitive information (i.e., private and confidential information) recorded by VCD's, monitoring devices and companion robots are limited. A VCD may temporarily record information while performing a task and subsequently delete the information once the task is completed. VCD's that operate intermittently may only record and store information during the period which they are activated. VCD's that operate intermittently pose less information privacy and confidentiality issues since a user is likely to be more cognizant when the VCD is active. Furthermore, the potential window for recording information is limited to the period of time during which the VCD remains activated. On the other hand, VCD's that operate continuously pose greater information privacy and confidentiality issues since these devices may, at any given time, record and store all verbal communications. Accordingly, these devices may record information that is intended to remain private. Similarly, an individual may be unaware of or simply forget that a VCD is activated. This can ultimately lead to inadvertently divulging what would otherwise be sensitive information. These privacy and confidentiality challenges also apply to monitoring devices and companion devices, which have the potential to collect and store sensitive information without being prompted by a voice command.

Embodiments of the present invention recognize that conversations are dynamic and not monotonic. Thus, what is deemed to be sensitive information can change between conversational topics, as well as between individual participants of a conversation. Similarly, embodiments of the present invention recognize that sensitive information is subjective. Accordingly, embodiments of the present invention provide for an adaptable, policy driven sanitation of sensitive information recorded and stored by voice application devices. Embodiments of the present invention further recognize that multiple instances, as well as different levels of sensitive information can occur within a single conversational topic. Accordingly, embodiments of the present invention provide for a policy driven hierarchical approach to protecting different classes or types of sensitive information. Embodiments of the present invention further recognize that sensitive information can be deduced from contextual clues. Accordingly, embodiments of the present invention provide for the protection of contextually sensitive information, and not just particular keywords or phrases.

Embodiments of the present invention further recognize that current methods for protecting sensitive information recorded by voice command applications may completely render data un-retrievable due to information privacy issues. Removing an entire passage simply because a key phrase or term is identified as sensitive renders any additional non-sensitive information unavailable for further use. For example, in a healthcare setting, health related information should remain protected, but at the same time be available for later use. Similarly, when retrieving sensitive information, only certain entities should be allowed to have access to the information.

Embodiments of the present invention provide for the selective protection of recorded communications that contain sensitive information based on individual privacy preferences, thereby allowing information recorded by voice application devices to be archived for later retrieval and analysis. For example, storing curated information may allow for accountability, archiving, machine learning training or debugging an application. In embodiments of the invention, protected communications recorded by voice application devices are securely stored (e.g., through encryption) to prevent access to sensitive information from untrusted third parties. However, the same protected communications can be selectively shared between particular entities and individuals (e.g., through access permissions).

Furthermore, embodiments of the present invention recognize that a conversation can be stored multiple times in different mediums (e.g., an audio file and a transcript of the same conversation). Accordingly, embodiments of the present invention provide for different types of protective actions for the same protective piece based on the type of medium in which the protected piece is stored.

Referring now to various embodiments of the invention in more detail, FIG. 1 is a functional block diagram of a computing environment, generally designated 100, suitable for operation of a privacy preserving program 102 in accordance with at least one embodiment of the invention. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Computing environment 100 includes computer system 104, user device 106, sanitation policy 108, and protection map 110 interconnected over network 112. Network 112 can be, for example, a telecommunications network, a local area network (LAN), a wide area network (WAN), such as the Internet, or a combination of the three, and can include wired, wireless, or fiber optic connections. Network 112 may include one or more wired and/or wireless networks that are capable of receiving and transmitting data, voice, and/or video signals, including multimedia signals that include voice, data, and video information. In general, network 112 may be any combination of connections and protocols that will support communications between computer system 104, user device 106, sanitation policy 108, protection map 110, and other computing devices (not shown) within computing environment 100.

Computer system 104 can be a standalone computing device, a management server, a web server, a mobile computing device, or any other electronic device or computing system capable of receiving, sending, and processing data. In other embodiments, computer system 104 can represent a server computing system utilizing multiple computers as a server system, such as in a cloud computing environment. In an embodiment, computer system 104 represents a computing system utilizing clustered computers and components (e.g., database server computers, application server computers, etc.) that act as a single pool of seamless resources when accessed within computing environment 100. Computer system 104 includes privacy preserving program 102. Computer system 104 may include internal and external hardware components, as depicted and described in further detail with respect to FIG. 3.

User device 106 can be a laptop computer, tablet computer, smartphone, smartwatch, or any programmable electronic device capable of communicating with various components and devices within computing environment 100, via network 112. In embodiments of the invention, at least one user device 106 is a voice application device. In general, user device 106 represents any programmable electronic devices or combination of programmable electronic devices capable of executing machine readable program instructions and communicating with other computing devices (not shown) within computing environment 100 via a network, such as network 112.

User device 106 includes user interface 114. User interface 114 provides an interface between each user device 106 and computer system 104. In one embodiment, user interface 114 may be a graphical user interface (GUI) or a web user interface (WUI) and can display text, documents, web browser windows, user options, application interfaces, and instructions for operation, and include the information (such a graphic, text, and sound) that a program present to a user and the control sequences the user employs to control the program. In another embodiment, user interface 114 may also be mobile application software that provides an interface between each the user device 106 and computer system 104. Mobile application software, or an "app", is a computer program that runs on smartphones, tablet computers, smartwatches and other mobile devices. In some embodiments, an individual communicates with a voice application device via verbal communications. In some embodiments, an individual communicates with a voice application device via user device 106. In these embodiments, a user of user device 106 utilizes user interface 114 to transmit audio, text, video, and/or images between user device 106 and a physically distinct voice application device.

Sanitation policy 108 defines the types of information that an individual considers to be sensitive, as well under which circumstances information should be regarded as sensitive. More specifically, sanitation policy 108 includes a categorical framework for identifying different types of sensitive information (i.e., protected pieces) divulged during a conversation, as well as the type of protective action to be performed for each type of protected piece identified. Embodiments of the present invention recognize that what is considered to be sensitive information is dynamic, such that types of sensitive information can change based on individual preferences and the contexts surrounding a verbal communication or conversation. Accordingly, sanitation policy 108 can be customized based on individual privacy and confidentiality preferences. In some embodiments, sanitation policy 108 is created and/or modified based on user input. In some embodiments, sanitation policy 108 is created and/or modified based on crowdsourcing. In some embodiments, sanitation policy 108 is created and/or modified based on previously stored conversation data. For example, privacy preserving program 102 uses machine learning software in combination with previously stored conversation data to modify or define on-the-fly sanitation policy 108.

In embodiments of the invention, privacy preserving program 102 monitors a conversation for information corresponding to each type of protected piece included in sanitation policy 108. In embodiments of the invention, a conversation can be recorded and stored in one or more different types of mediums. For example, a voice application device may record a conversation as an audio file, a video file, or both. In another example, a conversation recorded as an audio file may subsequently be converted into a corresponding transcript. Accordingly, in embodiments of the invention, privacy preserving program 102 monitors each type of conversational medium for each type of protected piece included in sanitation policy 108.

In embodiments of the invention, a protected piece can be based on one or more types of information. In some embodiments, a protected piece is identified based on a word, phrase, sentence, or conversational passage. In some embodiments, a protected piece is a keyword (e.g., social security number, bank account number, credit card number, address, etc.). In some embodiments, a protected piece is based on a context of a verbal communication or conversation. Context may include, but is not limited to a topic or theme of a verbal communication or conversation. For example, medical information, location information, relationship information, and financial information are all different types of sensitive information. Similarly, the location or time when a verbal communication or conversation takes, speaker identity, the number of speakers (e.g., a solo individual or a group), and speaker age also may contribute to what is considered to be sensitive information.

In an embodiment, a protected piece is based on a decibel level of an audio communication. In this embodiment, an audio communication is determined to be a protected piece if the decibel level of an audio communication falls below a given threshold level. For example, if an individual is speaking quietly or whispering (i.e., speaking at a low decibel level), it may indicate that the individual is disclosing sensitive information. On the other hand, if an individual is speaking loudly (i.e., speaking at a high decibel level), it may indicate that the individual is disclosing non-sensitive information. In an embodiment, a protected piece is based on non-verbal sounds. For example, Dan may not want any verbal communications or conversations that take place in his office to be recorded by a voice application device. In this example, privacy preserving program 102 detects the sound of typing. The sound of typing may be indicative that Dan is in his office. Accordingly, any verbal communications or conversations that take place while Dan is typing will not be recorded.

In an embodiment, a protected piece is based on prosodic characteristics of speech, such as intonation, tone, stress, rhythm, and emotional state. In an embodiment, a protected piece is determined based on a type of dialog act corresponding to the speech. A dialog act may relate to a speaker's intention (e.g., question, request, suggestion, agreement, statement, etc.).

In some embodiments, privacy preserving program 102 assigns one or more confidence scores to each protected piece identified. Here, a confidence score may be generally understood as a level of confidence that a verbal communication includes a particular type of sensitive information. In an embodiment, if a confidence score associated with a protected piece is below a given threshold, a user is notified that further action and/or confirmation is required. In an embodiment, privacy preserving program 102 updates or adjusts the confidence score based on information received from a user in response to the notification.

In embodiments of the invention, sanitation policy 108 includes a plurality of protection actions. A protection action may generally be understood as a method of protecting sensitive information from unwanted disclosure. It should be appreciated that the type of protection action used for each protected piece is dynamic, such that the type of protection action can change based on individual preferences.

Examples of protection actions may include, but are not limited to generalization, suppression, encryption, and sound shredding. In some embodiments, each type of sensitive information associated with a protected piece has a corresponding protection action. In some embodiments, a type of protection action is determined based on a confidence score associated with a protected piece.

Protection map 110 is a framework to identify the position of each protected piece of a conversation stored in one or more different mediums. More specifically, protection map 110 includes a uniform index that allows for the identification of the position of the same protected piece within different mediums. Protection map 110 further includes pointers that delimit each protected piece. For example, if a protected piece is identified in an audio communication, the pointers act as a reference to the portion of an audio file that includes the protected piece (e.g., an audio time stamp). In another example, if the same protected piece is identified in a text file, such as an audio transcript, the pointers act as a reference to the portion of text that includes the protected piece (e.g., a range of text bytes or page, column, and line number).

In embodiments of the invention, privacy preserving program 102 stores confidence scores corresponding to a type of sensitive information associated with a protected piece in protection map 110. In some embodiments, privacy preserving program 102 uses protection map 110 to identify conflicts between the same protected piece stored in different mediums. In some embodiments, privacy preserving program 102 uses protection map 110 to identify conflicts between two or more protected pieces located in the same portion of the same medium. In embodiments of the invention, protection map 110 stores contextual information associated with a conversation that includes a protective piece, as well as the type of protective piece included in the conversation.

Figure 2:
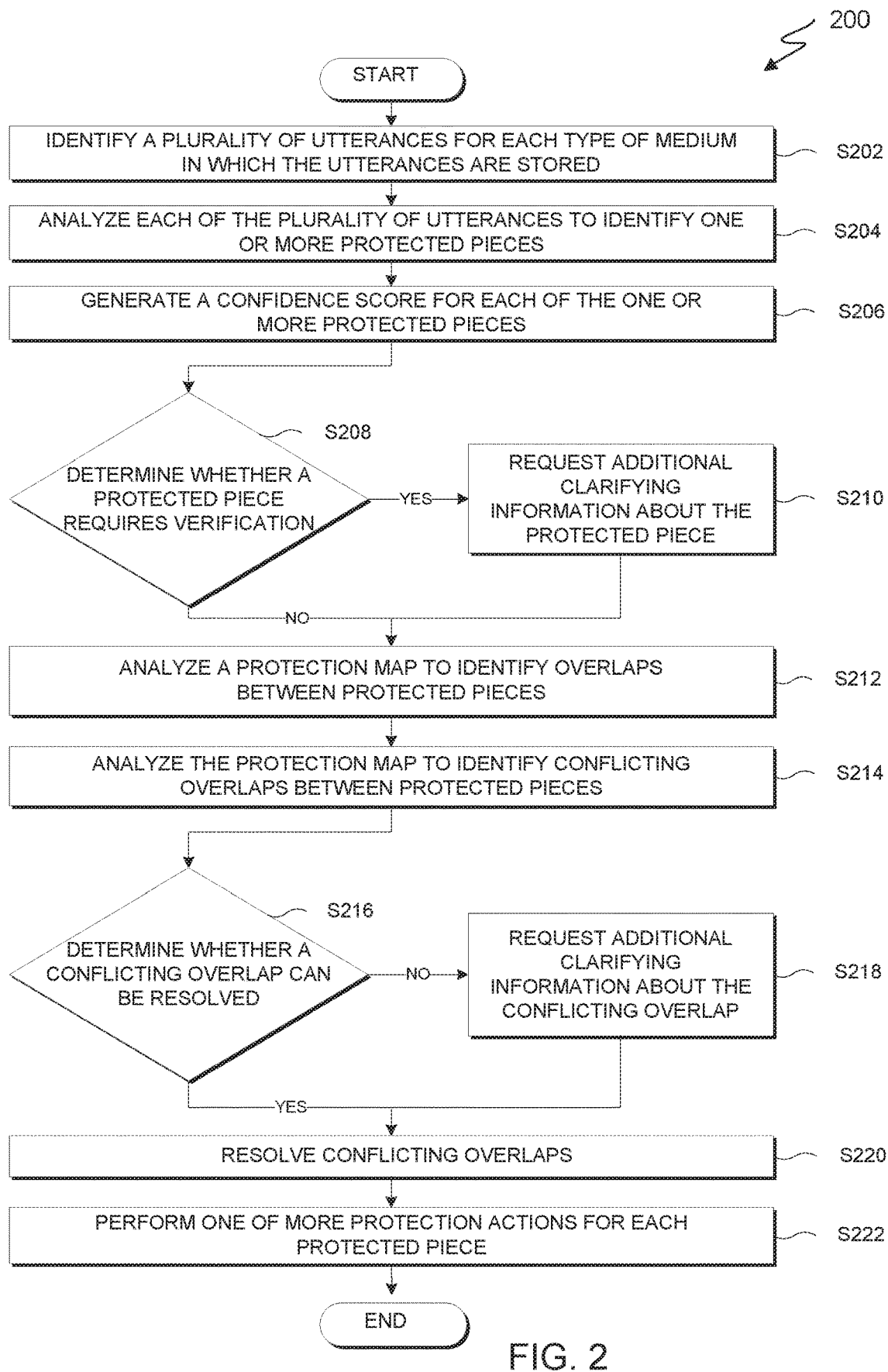
FIG. 2 is a flow chart diagram depicting operational steps for a privacy preserving program in accordance with at least one embodiment of the invention.

FIG. 2 is a flow chart diagram depicting operational steps for a privacy preserving program in accordance with at least one embodiment of the invention. It should be appreciated that embodiments of the present invention provide for the identification and protection of sensitive information recorded by voice control devices based on an adaptable, policy driven framework. FIG. 2 provides only an illustration of one implementation and does not imply any limitations with regard to the environments in which different embodiments may be implemented. Many modifications to the depicted environment may be made by those skilled in the art without departing from the scope of the invention as recited by the claims.

At step S202, privacy preserving program 102 identifies a plurality of utterances recorded by a voice application device, such as user device 106. An utterance may generally be understood as a verbal communication (e.g., word or statement), non-lexical communication (e.g., exclamations, sighs, laughs, cries, and shouts), or background noise. In embodiments of the invention, utterances can be recorded and stored in one or more different types of mediums (e.g., audio, video, and text). Accordingly, privacy preserving program 102 identifies a plurality of utterances for each type of medium in which the utterances are stored.

In some embodiments, privacy preserving program 102 identifies utterances based on converting audio signals into text. In these embodiments, privacy preserving program 102 converts audio signals into text using speech-to-text (STT) software. In an embodiment, the text is converted into a Unicode format (i.e., a universal encoding standard used for representing text for computer processing). In an embodiment, the text is converted into a speech synthesis mark-up language (SSML) format. In an embodiment, the raw text containing symbols (e.g., numbers and abbreviations) is converted into the equivalent of written-out words through text normalization (i.e., pre-processing or tokenization).

In some embodiments, privacy preserving program 102 identifies utterances without the use of STT software or natural language processing (NLP) software. In these embodiments, privacy preserving program uses automatic speech recognition (ASR) software to identify utterances. ASR software breaks down each utterance into phonemes. Each phoneme is then analyzed in sequence. In an embodiment, privacy preserving program 102 generates an acoustic model that textually represents the relationship between each audio signal and the phonemes or other linguistic units that make up speech. The acoustic model includes statistical representations of the sounds that make up each word.

In some embodiments, privacy preserving program 102 identifies utterances based on comparing sounds corresponding to each audio signal with word sequences. More specifically, privacy preserving program 102 compares sounds corresponding to each audio input to a language model. A language model provides context to distinguish between words and phrases that sound similar (e.g. "recognize speech" and "wreck a nice beach" are pronounced similarly but have very different meanings"). In an embodiment, privacy preserving software 102 compares sounds corresponding to each utterance to a positional language model. A positional language model describes the probability of given words occurring close to one another, but not necessarily immediately adjacent, in a text.

In an embodiment, privacy protection software 102 segments each audio signal into one or more of the following speech units: phones, diphones, half-phones, syllables, morphemes, words, phrases, and sentences. In an embodiment, privacy preserving program 102 determines intonational attributes associated with the utterances. Intonational attributes may include, but are not limited to pitch envelope (i.e., a combination of the speaker's fundamental frequency, pitch range, and the shape and timing of the pitch contour), overall speech rate, utterance timing (i.e., duration of segments and pauses), vocal quality, and intensity (i.e., loudness).

In some embodiments, identifying a plurality of utterances includes dividing the plurality of utterances into sets of utterances. Here, privacy preserving program 102 divides utterances into sets of utterances for each type of medium in which the utterances are stored. In some embodiments, each set of utterances is divided based on a speaker's vocal identity. In an embodiment, privacy preserving program 102 uses speaker diarisation software to identify when the same individual is speaking. Diarisation is the process of segmenting an audio signal into homogenous segments according to the speaker identity. Speaker diarisation includes speaker segmentation (i.e., finding speaker change points in an audio stream) and speaker clustering (i.e., grouping together speech segments based on intonational attributes). In some embodiments, each set of utterances is divided based on a telecommunications line from which an audio signal carrying the set of utterances is transmitted.

In some embodiments, privacy preserving program 102 identifies an identity associated with each set of utterances. In an embodiment, privacy preserving program 102 uses speaker verification software to verify an identity of a speaker associated with a set of utterances. Here, a speech sample (i.e., utterance) is compared against a previously created voice signature (i.e., voice print, template, or model). In an embodiment, privacy preserving program 102 uses voice recognition software (i.e., speaker identification software) to identify an identity of a speaker associated with a set of utterances. Speaker identification software identifies a speaker based on unique characteristics included within a speech sample. The speech sample is compared against multiple voice prints in order to determine the best match. For example, privacy preserving program 102 retrieves labeled training data (i.e., known vocal samples) of intonational attributes associated with previously recorded audio from various individuals. Based on matching the intonational attributes of a known vocal sample with the intonational attributes associated with a portion of the utterances stored by a VCD, a speaker's identity can be identified. In an embodiment, privacy protection program 102 uses a Gaussian mixture speaker model to identify an identity of a speaker associated with a set of utterances.

In some embodiments, privacy preserving program 102 identifies an identity of a speaker associated with a set of utterances via facial recognition software. For example, privacy preserving program 102 captures an image of a speaker via a camera built into user devices 106. In another example, privacy preserving program 102 breaks down video received from a recording device built into user device 102 into multiple video frames. In these embodiments, privacy preserving program 102 employs a speaker image dataset and image analysis software (i.e., comparing selected facial features from the image or video frame with facial features corresponding to the speaker image dataset) to identify a speaker.

At step S204, privacy preserving program 102 analyzes each set of utterances to identify one or more protected pieces. In some embodiments, privacy preserving program 102 analyzes each set of utterances in accordance with a single sanitation policy. In some embodiments, privacy preserving program 102 analyzes each set of utterances in accordance with a distinct sanitation policy. Here, each sanitation policy corresponds to a particular individual. In embodiments of the invention, each set of utterances may be recorded or stored in one or more different mediums. Accordingly, for each medium, privacy preserving program 102 individually analyzes the same set of utterances.

In some embodiments, privacy preserving program 102 identifies a protected piece based on keyword detection software. In an embodiment, privacy preserving program identifies a protected piece based on text-based keyword detection software. Here, each set of utterances is transcribed into text through STT software and keywords are identified based on comparing a list of keywords associated with sanitation policy 108 to the words included in the text. In an embodiment, privacy preserving program 102 identifies a protected piece based on acoustic keyword detection software. Here, protected pieces are identified based on comparing the linguistic units corresponding to a list of keywords associated with sanitation policy 108 to the linguistic units that make up each set of utterances. In an embodiment, privacy preserving program 102 identifies a protected piece based on phonetic-based keyword detection software. Here, protected pieces are identified based on comparing phoneme sequences corresponding to a list of keywords associated with sanitation policy 108 with phoneme sequences that make up each set of utterances.

In some embodiments, privacy preserving program 102 identifies a protected piece based on a determining a context associated with each set of utterances. In these embodiments, privacy preserving program 102 compares contextual information associated with a set of utterances to contextual information associated with sanitation policy 108. In an embodiment, privacy preserving program 102 determines a context through the use of text mining software to extract keywords corresponding to each set of utterances. Text mining (i.e., text data mining, text analytics) is the process of deriving high-quality information from text. Within the field of text mining, keyword extraction is the automatic identification of terms that best describe or characterize the subject of a text document. Here, each set of utterances is transcribed into text through STT software and keywords are identified within the transcribed text document. In some embodiments, privacy preserving program 102 determines a context through the use of speech analytics software (i.e., audio mining software) to spot keywords and phrases from a set of utterances. Here, phoneme sequences corresponding to the set of utterances are matched with phoneme sequence of known words. It should be appreciated that by using intermediate representations (including, but not limited to phonetic posteriorgrams and lattice representations) to match phoneme sequences, a context may be determined without requiring the use of STT software.

In some embodiments, privacy preserving program 102 identifies a protected piece based on determining a location from which a set of utterances is generated. In these embodiments, a protected piece includes any verbal communications generated from a particular location in accordance with protected location information stored in sanitation policy 108. In an embodiment, privacy preserving program 102 uses micro-location enabling technologies, such as Bluetooth Low Energy (BLE) based beacons, Radio Frequency Identification (RFID), and Near-Field Communication (NFC) to detect the presence of user device 106 within a location of a VDC. In an embodiment, privacy preserving program 102 uses a global positioning system (GPS) or wi-fi triangulation to determine the location of a VDC.

In some embodiments, privacy preserving program 102 identifies a protected piece based on determining a topic or theme of a conversation corresponding to a plurality of utterances. In an embodiment, a current topic of discussion is determined based, at least in part, through the use of speech analytics software. Speech analytics software is the process of analyzing categorical topics of discussion by isolating words and phrases that are most frequently used within a given time period and indicating whether the usage is trending up or down. For example, if the term "doctor" or "treatment" is identified from the plurality of utterances more than five times within a one minute time period, privacy preserving program 102 may determine that the current topic of discussion revolves around medical information.

At step S206, privacy preserving program 102 generates one or more confidence scores for each protected piece identified. Embodiments of the present invention recognize that certain types of sensitive information may not be as easily discernible as others. Accordingly, the generation of a confidence score ensures for the proper association of each protective piece identified with a particular type of sensitive information. This is important since different types of sensitive information may require a different type of protection action. Thus, the generation of a confidence score further ensures that the proper protection action is applied to a particular type of sensitive information.

A confidence score is a weighted score that indicates a level of confidence that a protected piece is associated with a particular type of sensitive information. In some embodiments, privacy preserving program 102 uses machine learning to determine a type of sensitive information associated with a protected piece. In these embodiments, privacy preserving program 102 generates a confidence score based on a degree of associativity between a protected piece and a labeled training set of data corresponding to a particular type of sensitive information. The higher the confidence score, the more likely that a protected piece is associated with a particular type of sensitive information. The lower the confidence score, the less likely that a protected piece is associated with a particular type of protected piece. In some embodiments, a protected piece is associated with a particular type of sensitive information if a confidence score is above a given threshold level.

In some embodiments, privacy preserving program 102 generates one or more confidence scores for the same protected piece stored in different mediums. Here, each confidence score corresponds to a level of confidence that a protected piece stored in a particular medium is associated with a particular type of sensitive information. For example, privacy preserving program 102 identifies the protected piece "medical information" divulged during a conversation. In this example, the conversation was recorded and stored as an audio file and a video file. Furthermore, the audio file was converted into a corresponding text file (e.g., a transcript of the conversation). Here, privacy preserving program 102 generates three confidence scores (one for each medium) for the protected piece "medical information." In some embodiments, privacy preserving program 102 generates a single, overall confidence score for the same protected piece stored in multiple mediums.

At decision step S208, privacy preserving program 102 determines whether a protected piece requires verification. Here, privacy preserving program 102 verifies that a protected piece is associated with a particular type of sensitive information. In some embodiments, verification is required for a protected piece based on generating a confidence score below a given threshold level. If verification is required, privacy preserving program 102 proceeds to step S210 (decision step "YES" branch). If verification is not required, privacy preserving program 102 proceeds to step S212 (decision step "NO" branch).

At step S210, responsive to a determination that verification is required, privacy preserving program requests additional clarifying information about the protected piece. In some embodiments, privacy preserving program 102 utilizes additional information in order to adjust or increase the confidence score associated with a protected piece that has a confidence score below a given threshold. In some embodiments, privacy preserving program 102 uses additional clarifying information to update sanitation policy 108. It should be appreciated that by updating sanitation policy 108 based on additional clarifying information, privacy preserving program 102 can more accurately determine a type of protected category associated with similar information in future verbal communications. Accordingly, the need for interrupting a user to request additional clarifying information will ultimately be reduced if higher confidence scores are generated.

In some embodiments, privacy preserving program 102 requests additional clarifying information upon initially detecting a protected piece within a conversation. In some embodiments, privacy preserving program 102 requests additional clarifying information upon detecting the end of a conversation. In some embodiments, privacy preserving program 102 requests additional clarifying information based on a verbal communication. For example, a user device 106, such as a VCD, initiates the following questions: "Does this portion of the conversation include sensitive information, and if so, what type of sensitive information?"

In some embodiments, privacy preserving program 102 requests additional clarifying information based on communicating with a user via user interface 114 of a user device 106. For example, privacy preserving program 102 request additional clarifying information based on a written communication, such as a text message. In these embodiments, a user may also be presented with a text transcript of the portion of a verbal communication in question. The user may further be provided with an option to confirm, select, or input a type of sensitive information associated with a protected piece. In some embodiments, privacy preserving program 102 does not request additional clarifying information. Instead, privacy preserving program 102 issues or displays a non-intrusive alert, such as a blinking light or an audible sound, via user device 106. A non-intrusive alert notifies a user that the user is currently divulging sensitive information.

At step S212, privacy preserving program 102 analyzes protection map 110 to identify overlaps between protected pieces. An overlap may generally be understood as a portion of a verbal communication or conversation that includes two or more protected pieces. In embodiments of the invention, privacy preserving program 102 identifies overlaps between protected pieces based on comparing a first pair of pointers associated with a first protected piece and a second pair of pointers associated with a second protected piece. Each pair of pointers includes a first pointer indicating the start of information corresponding to a protected piece and a second pointer indicating the end of information corresponding to the protected piece.

In some embodiments, privacy preserving program 102 identifies a partial overlap between protected pieces. For example, a two-minute conversation between Aaron and Dan is recorded as an audio file by user device 106, such as a VCD. During the two-minute conversation, privacy preserving program 102 determines a first protected piece (e.g., medical information) and a second protected piece (e.g., financial information). Furthermore, privacy preserving program 102 determines that the first protected piece begins at 00:00:15 and ends at 00:01:15. Similarly, privacy preserving program 102 determines that the second protected piece begins at 00:00:55 and ends at 00:01:35. Accordingly, a partial overlap between the first protected piece and the second protected piece occurs between 00:00:55 and 00:01:15 of the audio file.

In some embodiments, privacy preserving program 102 identifies a complete overlap between protected pieces. For example, a five-minute conversation between Lauren and Mary is recorded as an audio file by user device 106, such as a VCD. During the five-minute conversation, privacy preserving program 102 determines a first protected piece (e.g., medical information) and a second protected piece (e.g., address information). Furthermore, privacy preserving program 102 determines that the first protected piece begins at 00:00:30 and ends at 00:00:4:30. Similarly, privacy preserving program 102 determines that the second protected piece begins at 00:01:30 and ends at 00:02:00. Accordingly, a complete overlap between the first protected piece and the second protected piece occurs between 00:001:30 and 00:02:00 of the audio file.

At step 214, privacy preserving program 102 analyzes protection map 110 to identify conflicting overlaps between protected pieces. A conflicting overlap occurs when two or more overlapping protected pieces each have a corresponding protection action that conflicts with one another. Continuing with the previous example, privacy preserving program 102 identified a conflicting overlap between the first protected piece and the second protected piece from 00:001:30 to 00:02:00 of the audio file. In this example, privacy preserving program 102 determines that the first protected piece is associated with a first type of sensitive information (e.g., "medical information"). In accordance with sanitation policy 108, medical information is protected by the protection action "generalization." Similarly, privacy preserving program 102 determines that the second protected piece is associated with a second type of sensitive information (e.g., "financial information). In accordance with sanitation policy 108, financial information is protected by the protection action "suppression." Accordingly, performing both the protection action "generalization" and the protection action "suppression" will result in conflicting (i.e., incompatible) protection actions for the same portion of the conversation. In other words, if the overlapping portion of the verbal communication is suppressed (i.e., entirely removed), then the same portion of the verbal communication that has been removed can no longer be generalized.

At decision step S216, privacy preserving program 102 determines whether a conflicting overlap can be resolved. If a conflicting overlap cannot be resolved, privacy preserving program 102 proceeds to step S218 ("decision step "NO" branch). If a conflicting overlap can be resolved, privacy preserving program 102 proceeds to step S220 (decision step "YES" branch).

At step S218, responsive to a determination that a conflicting overlap cannot be resolved, privacy preserving program 102 requests additional clarifying information about the conflicting overlap. In some embodiments, privacy preserving program 102 requests additional clarifying information about a conflicting overlap when privacy preserving program 102 is unable to resolve a conflicting overlap in accordance with sanitation policy 108. In embodiments of the invention, privacy preserving program 102 requests additional clarifying information similar to step S210. For example, user device 106, such as a VCD, initiates the following questions: "What type of protective action should be performed on this portion of the conversation." "What type of protection action should be performed on all of the protected pieces included in the conflicting overlap?" "Should all similar conversations be protected with this type of protective action?" Based on the additional clarifying information, privacy preserving program performs the same type of privacy action for each protective piece included in a conflicting overlap. In some embodiments, privacy preserving program 102 uses additional clarifying information about a conflicting overlap to update sanitation policy 108. It should be appreciated that by updating sanitation policy 108 based on additional clarifying information about a conflicting overlap, privacy preserving program 102 can better revolve conflicting overlaps between protected pieces in future verbal communications. Accordingly, the need for interrupting a user to request additional clarifying information in order to revolve a conflicting overlap will ultimately be reduced.

At step S220, privacy preserving program 102 resolves conflicting overlaps. In embodiments of the invention, privacy preserving program 102 resolves conflicting overlaps by determining a single protection action to be performed for each protected piece included in a conflicting overlap. In some embodiments, privacy preserving program 102 resolves a conflicting overlap based on confidence scores. Here, privacy preserving program 102 selects a protection action corresponding to a protected piece with the highest confidence score. In some embodiments, privacy preserving program 102 resolves a conflicting overlap based on a privacy protection hierarchy. A protection hierarchy identifies whether one particular protection action should take precedence over another. Here, privacy preserving program 102 selects a protection action corresponding to a protected piece with the highest preference. For example, protection actions are ranked in a hierarchical order based on a level or degree of protection. In some embodiments, privacy preserving program 102 resolves a conflicting overlap based on a default setting. For example, if privacy preserving program 102 identifies a conflicting overlap, the default setting for all conflicting overlaps is the protection action "suppression." In some embodiments, privacy preserving program 102 resolves conflicting overlaps based on additional clarifying information received in step S218.

At step S222, privacy preserving program 102 performs one or more protection actions for each protected piece identified. Here, privacy preserving program 102 modifies sensitive information associated with a verbal communication to form a modified conversation. A modified conversation may generally be understood as a conversation (existing in any type of medium) that is devoid of any sensitive information. For example, a modified conversation can exist in an audio, video, or textual format. Accordingly, a modified conversation only includes non-sensitive information associated with the conversation. It should be appreciated that the type of protection action to be performed on information associated with each protected piece may be customized, such that a type of protection action corresponding to different types of sensitive information can change based on individual preferences. Thus, the same conversation produced by two different individuals will result in two different modified conversations. Examples of protection actions may include, but are not limited to generalization, suppression, encryption, and sound shredding.

In embodiments of the invention, privacy preserving program 102 performs one or more protection actions for each protected piece identified in each medium. In some embodiments, sanitation policy 108 includes a list of types of sensitive information and a corresponding protection action for each type of sensitive information. Here, privacy preserving program 102 performs a protection action based on associating a protective piece with a particular type of sensitive information. Depending on the type of medium in which a protected piece exists, privacy preserving program 102 may perform a different protective action for the same protected piece. For example, privacy preserving program 102 performs a first type of protection action for a protected piece associated with a verbal communication recorded or stored as an audio file. However, privacy preserving program 102 performs a second type of protection action for the same protected piece associated with a text transcript generated from the audio file of the same verbal communication.

In embodiments of the invention, privacy preserving program 102 stores modified conversations for later retrieval and analysis. In some embodiments, privacy preserving program 102 predicts additional types of information that an individual may consider sensitive based on previously stored modified conversations. Embodiments of the present invention recognize that certain types of sensitive information, that an individual would otherwise want to be protected, may not have been originally contemplated, and thus are absent from sanitation policy 108. In an embodiment, privacy preserving program 102 uses concept expansion software in combination with previously stored modified conversations (i.e., semantic lexicon induction software or semantic set expansion software) to infer additional types of information that an individual may regard as sensitive. In some embodiments, privacy preserving program 102 performs data analytics on previously stored modified conversations. This will ultimately allow voice application devices to better target individual preferences, provide personalized recommendations, advertisements, sales, and promotions when interacting with a user.

In some embodiments, privacy preserving program 102 uses previously stored modified conversations to learn what types of information an individual considers to be sensitive. Embodiments of the present inventions recognize that VCD's are not only capable of receiving and storing verbal communications, but are further capable of responding to verbal communications, providing feedback, or otherwise generally imitating a natural voice conversation based, in part, on recorded communications. These prior recorded communications will likely include sensitive information. Accordingly, VCD's also have the potential to divulge sensitive information when communicating with a user. In these embodiments, privacy preserving program 102 uses knowledge based learning software in combination with previously stored modified conversations to more accurately determine under which circumstances particular types of sensitive information should not be divulged, as well as which types of sensitive information should not be divulged under any circumstances. Understanding and learning when and what information can and cannot divulged is especially important with VCD's that operate continuously.

Figure 3:
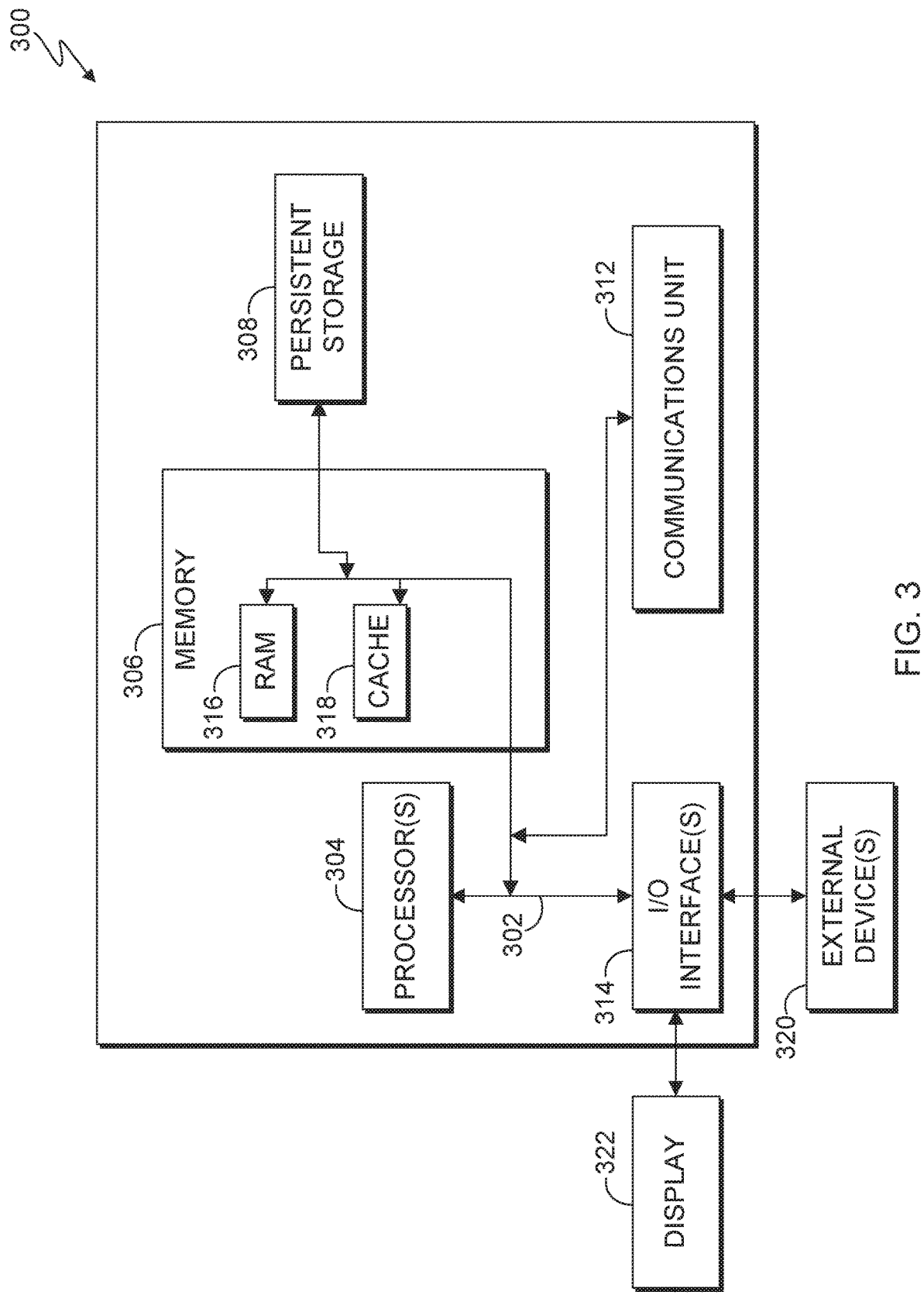
FIG. 3 is a block diagram depicting components of a computer suitable for executing a privacy preserving program in accordance with at least one embodiment of the invention.

FIG. 3 is a block diagram depicting components of a computer 300 suitable for privacy preserving program 102, in accordance with at least one embodiment of the invention. FIG. 3 displays the computer 300, one or more processor(s) 304 (including one or more computer processors), a communications fabric 302, a memory 306 including, a RAM 316, and a cache 318, a persistent storage 308, a communications unit 312, I/O interfaces 314, a display 322, and external devices 320. It should be appreciated that FIG. 3 provides only an illustration of one embodiment and does not imply any limitations with regard to the environments in which different embodiments may be implemented. Many modifications to the depicted environment may be made.

As depicted, the computer 300 operates over the communications fabric 302, which provides communications between the computer processor(s) 304, memory 306, persistent storage 308, communications unit 312, and input/output (I/O) interface(s) 314. The communications fabric 302 may be implemented with any architecture suitable for passing data or control information between the processors 304 (e.g., microprocessors, communications processors, and network processors), the memory 306, the external devices 320, and any other hardware components within a system. For example, the communications fabric 302 may be implemented with one or more buses.

The memory 306 and persistent storage 308 are computer readable storage media. In the depicted embodiment, the memory 306 comprises a random access memory (RAM) 316 and a cache 318. In general, the memory 306 may comprise any suitable volatile or non-volatile one or more computer readable storage media.

Program instructions for privacy preserving program 102 may be stored in the persistent storage 308, or more generally, any computer readable storage media, for execution by one or more of the respective computer processors 304 via one or more memories of the memory 306. The persistent storage 308 may be a magnetic hard disk drive, a solid state disk drive, a semiconductor storage device, read-only memory (ROM), electronically erasable programmable read-only memory (EEPROM), flash memory, or any other computer readable storage media that is capable of storing program instructions or digital information.

The media used by the persistent storage 308 may also be removable. For example, a removable hard drive may be used for persistent storage 308. Other examples include optical and magnetic disks, thumb drives, and smart cards that are inserted into a drive for transfer onto another computer readable storage medium that is also part of the persistent storage 308.

The communications unit 312, in these examples, provides for communications with other data processing systems or devices. In these examples, the communications unit 312 may comprise one or more network interface cards. The communications unit 312 may provide communications through the use of either or both physical and wireless communications links. In the context of some embodiments of the present invention, the source of the various input data may be physically remote to the computer 300 such that the input data may be received and the output similarly transmitted via the communications unit 312.

The I/O interface(s) 314 allow for input and output of data with other devices that may operate in conjunction with the computer 300. For example, the I/O interface 314 may provide a connection to the external devices 320, which may be as a keyboard, keypad, a touch screen, or other suitable input devices. External devices 320 may also include portable computer readable storage media, for example thumb drives, portable optical or magnetic disks, and memory cards. Software and data used to practice embodiments of the present invention may be stored on such portable computer readable storage media and may be loaded onto the persistent storage 308 via the I/O interface(s) 314. The I/O interface(s) 314 may similarly connect to a display 322. The display 322 provides a mechanism to display data to a user and may be, for example, a computer monitor.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of computer program instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
    identifying a first protected piece from a conversation, wherein the first protected piece corresponds to a portion of the conversation that includes sensitive information;
    selecting, from a plurality of types of protection actions, a first type of protection action for the first protected piece, wherein a type of sensitive information associated with the first protected piece and a type of medium in which the protected piece is stored indicates from which of the plurality of types of protection actions to select; and
    performing the first type of protection action on the first protected piece to form a modified conversation, wherein the modified conversation is devoid of the sensitive information.

2. The computer-implemented method of claim 1, further comprising:
    requesting additional clarifying information about the first protected piece based on a confidence score associated with the first protected piece falling below a given threshold level;

adjusting the confidence score, in response to receiving the additional clarifying information, to form an adjusted confidence score; and determining that the first protected piece is associated with the first type of sensitive information based on the adjusted confidence score exceeding the given threshold level.

3. The computer-implemented method of claim 1, further comprising:

identifying a first portion of the conversation corresponding to the first protected piece;

identifying a second portion of the conversation corresponding to a second protected piece; and determining that the first portion corresponding to the first protected piece and the second portion corresponding to the second protected piece overlap.

4. The computer-implemented method of claim 3, further comprising determining a conflicting overlap based, at least in part, on:

identifying the first type of protection action for the first protected piece;

identifying a second type of protection action for the second protected piece; and determining that the first type of protection action and the second type of protection action are incompatible.

5. The computer-implemented method of claim 4, further comprising resolving the conflicting overlap based on:

determining that a first confidence score corresponding to the first protected piece is higher than a second confidence score corresponding to the second protected piece; and performing the first protection action for the first protected piece and the second protected piece based on the first protected piece having a higher confidence score.

6. The computer-implemented method of claim 4, further comprising resolving the conflicting overlap based on:

determining that a first hierarchical position corresponding to the first type of protection action is higher than a second hierarchical position corresponding to the second type of protection action; and performing the first type of protection action for the first protected piece and the second protected piece based on the first protected piece having a higher hierarchical position.

7. The computer-implemented method of claim 4, further comprising resolving the conflicting overlap based on:

requesting additional clarifying information about the conflicting overlap; and performing a same type of protection action for the first protected piece and the second protected piece based on the additional clarifying information.

8. A computer program product, the computer program product comprising one or more computer readable storage media and program instructions stored on the one or more computer readable storage media, the program instructions comprising instructions to:

identify a first protected piece from a conversation, wherein the first protected piece corresponds to a portion of the conversation that includes sensitive information;

select, from a plurality of types of protection actions, a first type of protection action for the first protected piece, wherein a type of sensitive information associated with the first protected piece and a type of medium in which the protected piece is stored indicates from which of the plurality of types of protection actions to select; and perform the first type of protection action on the first protected piece to form a modified conversation, wherein the modified conversation is devoid of the sensitive information.

9. The computer program product of claim 8, further comprising program instructions to:

request additional clarifying information about the first protected piece based on a confidence score associated with the first protected piece falling below a given threshold level;

adjust the confidence score, in response to receiving the additional clarifying information, to form an adjusted confidence score; and determine that the first protected piece is associated with the first type of sensitive information based on the adjusted confidence score exceeding the given threshold level.

10. The computer program product of claim 8, further comprising program instructions to:

identify a first portion of the conversation corresponding to the first protected piece;

identify a second portion of the conversation corresponding to a second protected piece; and determining that the first portion corresponding to the first protected piece and the second portion corresponding to the second protected piece overlap.

11. The computer program product of claim 10, further comprising determining a conflicting overlap based, at least in part, on program instructions to:

identify the first type of protection action for the first protected piece;

identify a second type of protection action for the second protected piece; and determine that the first type of protection action and the second type of protection action are incompatible.

12. The computer program product of claim 11, further comprising resolving the conflicting overlap based on program instructions to:

identify a highest confidence score between a first confidence score corresponding to the first protected piece and a second confidence score corresponding to the second protected piece; and perform a protection action corresponding to a protected piece with the highest confidence score for each of the first protected piece and the second protected piece.

13. The computer program product of claim 11, further comprising resolving the conflicting overlap based on program instructions to:

identify a highest hierarchical position between a first protection action corresponding to the first protected piece and a second protection action corresponding to the second protected piece; and perform a protection action with the highest hierarchical position for each of the first protected piece and the second protected piece.

14. The computer program product of claim 11, further comprising resolving the conflicting overlap based on program instructions to:

request additional clarifying information about the conflicting overlap; and perform a same type of protection action for the first protected piece and the second protected piece based on the additional clarifying information.

15. A computer system, comprising:
one or more computer processors;
one or more computer readable storage media;
computer program instructions;
the computer program instructions being stored on the one or more computer readable storage media for execution by the one or more computer processors; and
the computer program instructions comprising instructions to:
- identify a first protected piece from a conversation, wherein the first protected piece corresponds to a portion of the conversation that includes sensitive information;
- select, from a plurality of types of protection actions, a first type of protection action for the first protected piece, wherein a type of sensitive information associated with the first protected piece and a type of medium in which the protected piece is stored indicates from which of the plurality of types of protection actions to select; and
- perform the first type of protection action on the first protected piece to form a modified conversation, wherein the modified conversation is devoid of the sensitive information.

16. The computer system of claim 15, further comprising program instructions to:
- request additional clarifying information about the first protected piece based on a confidence score associated with the first protected piece falling below a given threshold level;
- adjust the confidence score, in response to receiving the additional clarifying information, to form an adjusted confidence score; and
- determine that the first protected piece is associated with the first type of sensitive information based on the adjusted confidence score exceeding the given threshold level.

17. The computer system of claim 15, further comprising program instructions to:
- identify a first portion of the conversation corresponding to the first protected piece;
- identify a second portion of the conversation corresponding to a second protected piece; and
- determining that the first portion corresponding to the first protected piece and the second portion corresponding to the second protected piece overlap.

* * * * *